United States Patent [19]

Harris et al.

[11] Patent Number: 4,743,450
[45] Date of Patent: May 10, 1988

[54] STABILIZED COMPOSITIONS

[75] Inventors: Michael Harris, Hackettstown; Gerard Hokanson, Long Valley; Kuchi Murthy, Morris Plains; Robert Reisch, Haledon; Frank Waldman, Wayne, all of N.J.

[73] Assignee: Warner-Lambert Company, Morris Plains, N.J.

[21] Appl. No.: 17,962

[22] Filed: Feb. 24, 1987

[51] Int. Cl.⁴ .................. A61K 31/195; A61K 31/40; A61K 31/27; A61K 31/505

[52] U.S. Cl. ..................................... 424/440; 424/465; 514/423

[58] Field of Search .................................. 424/440, 465

[56] References Cited

U.S. PATENT DOCUMENTS 4,656,188 4/1987 Veber et al. ..................... 514/562 X Primary Examiner—Michael R. Lusignan
Attorney, Agent, or Firm—Ronald A. Daignault

[57] ABSTRACT

The cyclization, hydrolysis, and coloration of certain ACE inhibitors is minimized when they are formulated with a metal-containing stabilizer and a saccharide.

17 Claims, No Drawings

STABILIZED COMPOSITIONS

BACKGROUND

Certain ACE (Angiotensin Converting Enzyme) inhibitors, which are useful as antihypertensives, are susceptible to certain types of degradation. Specifically, quinapril and structurally-related drugs can degrade via (1) cyclization via internal nucleophilic attack to form substituted diketopiperazines, (2) hydrolysis of the side-chain ester group, and (3) oxidation to form products having often unwanted coloration.

THE INVENTION

It has been discovered that stable compositions containing ACE inhibitors of the type discussed above can be produced using certain additives as stabilizers.

In one embodiment, 8.6 wt % magnesium carbonate is combined with 5.4 wt % quinapril hydrochloride with the inclusion of 38.0 wt % lactose to yield a composition which withstands oxidative, hydrolytic, and cyclization degradation at 60° C. for one month.

ADVANTAGES

The compositions of the invention have several advantages over compositions which do not contain the stabilizing additive(s) discussed herein. Principally, the active ingredients or drugs contained therein are virtually preserved from cyclization and hydrolysis. In addition, the discoloration which sometimes occurs when ACE inhibitors of this class are formulated and allowed to stand for significant periods of time is minimized or eliminated completely. Thus, a stable tabletted quinapril formulation can be produced which will undergo no detectable oxidative discoloration.

In addition to having greater storage stability, the instant formulations are rendered more suitable for use in drug combinations.

These and other advantages of the invention will become apparent from a consideration of the following description of the invention.

DESCRIPTION OF THE INVENTION

The invention deals with:

I. A pharmaceutical composition which contains:
  (a) a drug component which comprises an ACE inhibitor which is susceptible to cyclization, hydrolysis, and/or discoloration.
  (b) an amount of a stabilizer component or components suitable to retard cyclization, hydrolysis, and/or discoloration, and II. A process for stabilizing an ACE inhibitor drug which comprises the step of contacting the drug with:
  (a) an amount of stabilizer(s) suitable to retard cyclization and/or hydrolysis.

III. A method of making a pharmaceutical dosage form which comprises the step of including in the formulation suitable amounts of:
  (a) an ACE inhibitor, and
  (b) stabilizers which contain alkaline agents alone or alkaline agents in combination with saccharides (i.e., sugars) as one or more cyclization, hydrolysis, and discoloration inhibitor(s).

Preferably, the compositions and processes made and used in accordance with the invention will also contain one or more substances which do not interfere with the function of the stabilizing additive(s). Generally, lubricants, such as hydrogenated vegetable oils and talc, binders, such as gelatin, and/or disintegrants, such as polyplasdone, are suitable.

DRUG COMPONENT(S)

The compositions of the invention contain at least one ACE inhibitor and, optionally, one or more other medicament drugs or beneficial substances.

The ACE inhibitors which can be used in the invention are any of a group of well-known compounds which have antihypertensive properties.

One preferred group of compounds includes compounds conforming to the general formula

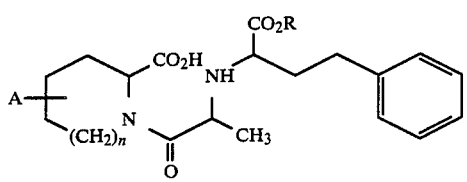

wherein A is absent, a fused five, six, or seven-membered cycloaliphatic ring or a fused benzene ring which is unsubstituted or substituted by one or two alkoxy groups having one to four carbon atoms; n is zero or one, and R is hydrogen or alkyl having one to five carbon atoms. Preferably A is absent, a fused five or six-membered cycloaliphatic ring or a fused benzene ring which is unsubstituted or substituted by two methoxy groups; n is zero or one, and R is hydrogen or ethyl.

Particularly valuable are enalapril, quinapril, or indolapril, their corresponding free acids or pharmaceutically acceptable acid addition or base salts thereof.

Compounds of this type are disclosed in U.S. Pat. Nos. 4,344,949, 4,374,829, and 4,425,355, the disclosure of which are hereby incorporated by reference.

The total drug content of the final composition will be about 1 to about 70%, preferably from about 1% to about 25%.

All percentages stated herein are weight percentages based on total composition weight, unless otherwise stated.

The daily dosages of the pharmaceutical preparations of the invention depend upon the nature of the dosage form, the nature of the drug(s) and the type and extent of any interactive(s), in drug combinations. Thus, the therapeutic needs of the individual patient and the desires of the prescribing physician dictate the dosage levels to be employed.

In general, however, the manufacturer's specifications for any drug or drug combination are useful guides to administration. *The Physicians Desk Reference* or other suitable publication can be consulted to ascertain appropriate dosase levels.

Nonetheless, typical dosage levels for quinapril and enalapril are from about 1 mg to about 80 mg per dosage.

Suitable categories of drugs that may be employed in addition to ACE inhibitors in the instant compositions may vary widely and generally represent any stable drug combination.

Illustrative categories and specific examples include:
(a) Diuretics, such as hydrochlorothiazide.
(b) Antitussives, such as dextromethorphan, dextromethorphan hydrobromide, noscapine, carbetapentane citrate, and chlophedianol hydrochloride;

(c) Antihistamines, such as chlorpheniramine maleate, phenindamine tartrate, pyrilamine maleate, doxylamine succinate, and phenyltoloxamine citrate, (d) Decongestants, such as phenylephedrine hydrochloride, phenylpropanolamine hydrochloride, pseudoephedrine hydrochloride, ephedrine; and (e) Various alkaloids, such as codeine phosphate, codeine sulfate, and morphine.

(f) Mineral supplements such as potassium chloride and the like.

The medicaments and/or other beneficial substances to be used herein may be selected from a wide variety of substances and pharmaceutically acceptable forms thereof, e.g., their acid addition salts. Both organic and inorganic salts may be used provided the drug maintains its medicament value. Exemplary acid salts include hydrochloride, hydrobromide, orthophosphate, benzoate, maleate, tartrate, succinate, citrate, salicylate, sulfate, acetate, and the like. Mixtures are operable.

One preferred group of drugs to be used in combination with ACE inhibitors includes: betablockers, diuretics, calcium blockers, and the like.

STABILIZER(S)

The cyclization and hydrolytic instability which are exhibited by certain of the drugs discussed above can be overcome via the use of a suitable quantity, i.e., an effective amount of an alkaline stabilizer, together with saccharides.

The alkaline stabilizers of the invention include the inorganic salts of metals of Groups I and II of the Periodic Table. Thus, salts of alkali and alkaline earth metals are operable. Magnesium, calcium, and sodium are preferred. Magnesium is most preferred.

The anionic portion of the salt employee may be any which does not deleteriously affect the stability of the overall formulation. Thus, borates, silicates, and carbonates are contemplated. Carbonates are preferred. Mixtures are operable.

The quantity of the stabilizer component to be used will lie between about 1% and 90%, preferably about 10% to about 80%. In general, any amount which will effectively retard or prevent degradation of the ACE inhibitor component(s) can be used.

SACCHARIDES

The saccharide components to be used in the pharmaceutical products and methods of the invention are substances which are compatible with the alkali or alkaline earth metal-containing stabilizers. Generally, they are substances which do not contain groups which could significantly interfere with the function of either the metal-containing component or the drug component. Mannitol, lactose, and other sugars are preferred. Mixtures are operable.

Generally, the quantity of saccharide present will be from about 5% to about 90%, preferably about 10% to about 80%.

EXCIPIENT(S)

The optional excipients which can be used in the instant compositions are also substances which must be compatible with the alkali or alkaline earth metal-containing stabilizers so that it does not interfere with its function in the composition.

The compositions of the invention may contain suitable quantities of disintegrating agents, carriers, diluents, pigments, binders, colorants, lubricants, and other additives conventionally used in the production of pharmaceutical products.

Useful disintegrating agents can be chosen from those generally found suitable in pharmaceutical preparations. Thus, modified starch, polyvinyl pyrrolidone (cross-linked or uncross-linked) and modified cellulose derivatives can be employed. Cross-linked polyvinylpyrrolidone is preferred. Mixtures are operable. The disintegrant component will generally comprise about 1% to about 15% of the total composition.

Useful lubricants include those generally used in pharmaceutical formulation to assist in the processing of one or more materials during the preparation of a final dosage form. Among the lubricants contemplated for use herein are stearates of magnesium, calcium or zinc, and hydrogenated vegetable oils. Magnesium stearate is a preferred lubricant. Mixtures are operable. The lubricant component will, when present, generally comprise from about 0.1 to about 5%, preferably about 0.5 to about 3% of the total composition.

The composition of the invention may also contain from about 1 to about 10%, preferably about 2 to about 7% of a binder. Useful binders include gelatin, polyvinylpyrrolidone, and the like. Gelatin is preferred. Mixtures are operable.

Any techniques for processing the products of the invention which are appropriate can be employed. A wet granulation process is preferred.

The percentages in which excipients are used are not critical. In general, their quantities will be consistent with the amount given above for the drug, stabilizer, and lubricant components, i.e., they make up the remainder of the composition.

DOSAGE FORMS

The final form of the pharmaceutical preparations made in accordance with the invention can vary greatly. Thus, tablets, capsules, sachets, sprinklers, pomades, transdermal compositions, buccal preparations, candy compositions, nasal formulations, ocular compositions, and the like are contemplated. Orally administrable forms, i.e., tablets, caplets, and capsules, are preferred.

Solid, semi-solid, and liquid formulations can be made. However, solids are highly preferred.

The drug preparations can be adapted for immediate, slow, or sustained release profiles, or any combination of these. Thus, a formulation adapted to give an initial loading dosage within 30 minutes followed by sustained release of the remaining drug over 4 to 12 hours is contemplated. Sustained and immediate release formulations are preferred.

Reasonable variations, such as those which would occur to a skilled artisan, can be made herein without departing from the scope of the invention.

EXAMPLE A

The following materials were combined by the wet granulation method for the manufacture of 5 mg tablets.

| | |
|---|---|
| Quinapril Hydrochloride | 5.4 mg |
| Magnesium Carbonate | 46.6 mg |
| Lactose | 38.0 mg |
| Gelatin | 5.0 mg |
| Polyplasdone | 4.0 mg |
| Magnesium Stearate | 1.0 mg |

EXAMPLE B

The following materials were processed by wet granulation for 40 mg tablets.

| | |
|---|---|
| Quinapril Hydrochloride | 43.4 mg |
| Magnesium Carbonate | 250.0 mg |
| Lactose | 66.6 mg |
| Gelatin | 20.0 mg |
| Polyplasdone | 16.0 mg |
| Magnesium Stearate | 40 mg |

EXAMPLE C

The following standard composition was processed for 5 mg tablets without the addition of a stabilizer of the present invention.

| | |
|---|---|
| Quinapril Hydrochloride | 5.425 g |
| Lactose Anhydrous | 119.575 g |
| Microcrystalline Cellulose | 14.775 g |
| Disodium EDTA | 0.225 g |
| Sterotex HM | 1.500 g |
| Syloid 244 Silica Gel | 3.000 g |
| Stearic Acid | 4.500 g |
| Ascorbic Acid USP | 1.000 g |
| Water, Purified USP | 2.250 g |

EXAMPLE D

The following materials were combined as in Example A for the manufacture of 5-mg tablets.

| | |
|---|---|
| Quinapril Hydrochloride | 5.4 mg |
| Magnesium Carbonate | 88.4 mg |
| Gelatin | 5.2 mg |
| Magnesium Stearate | 1.0 mg |

EXAMPLE E

Stability of the tablets prepared in the previous examples were tested at 60° C. for one month.

| | | Degradation Products (%) | |
|---|---|---|---|
| | Quinapril (%)[a] | Diketopiperazine | Hydrolysis Product |
| Example A | 97.1 | 0.7 | 2.0 |
| Example B | 98.1 | 0.6 | 1.2 |
| Example C[b] | 68.1 | 32.4 | <1 |
| Example D | 93.0 | 0.5 | 8.0 |

[a]Percent of original quinapril content.
[b]Analysis was carried out after five days at 60° C.

We claim:

1. A pharmaceutical composition which contains:
   (a) a drug component which comprises a suitable amount of an ACE inhibitor which is susceptible to cyclization, hydrolysis, and discoloration,
   (b) a suitable amount of an alkali or alkaline earth metal carbonate to inhibit cyclization and discoloration, and
   (c) a suitable amount of a saccharide to inhibit hydrolysis.

2. The composition of claim 1 wherein (a) is enalapril or a pharmaceutically acceptable acid addition salt thereof.

3. The composition of claim 1 wherein (a) contains at least one additional drug.

4. The composition of claim 1 wherein (b) contains magnesium carbonate.

5. The composition of claim 1 wherein (c) contains at least one of mannitol and lactose.

6. The composition of claim 1 wherein the composition also contains at least one material selected from the group consisting of: binders, disintegrants, and lubricants.

7. The composition of claim 1 wherein (a) is a compound of the formula

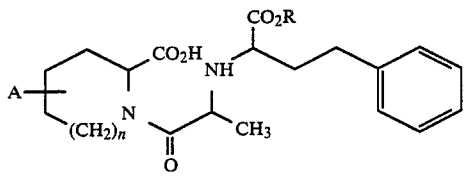

wherein A is absent, a fused five, six, or seven-membered cycloaliphatic ring or a fused benzene ring which is unsubstituted or substituted by one or two alkoxy groups having one to four carbon atoms; n is zero or one, and R is hydrogen or alkyl having one to five carbon atoms, or a pharmaceutically acceptable acid addition salt thereof.

8. The composition of claim 7 wherein A is absent, a fused five or six-membered cycloaliphatic ring or a fused benzene ring which is unsubstituted or substituted by two methoxy groups; n is zero or one; and R is hydrogen or ethyl, or a pharmaceutically acceptable acid addition salt thereof.

9. The composition of claim 1 wherein (a) is quinapril, or a pharmaceutically acceptable acid addition salt thereof.

10. The composition of claim 1 wherein (a) is quinapril hydrochloride.

11. The composition of claim 1 wherein (a) is indolapril or a pharmaceutically acceptable acid addition salt thereof.

12. A tablet containing the composition of claim 1.

13. A tablet containing the composition of claim 3.

14. A candy formulation containing the composition of claim 1.

15. A candy formulation containing the composition of claim 3.

16. A process for stabilizing an ACE inhibitor drug against cyclization which comprises the step of contacting the drug with:
   (a) a suitable amount of an alkali or alkaline earth-metal carbonate and,
   (b) one or more saccharides.

17. The process of claim 16 wherein the drug is selected from the group consisting of quinapril, enalapril, and indolapril, or a pharmaceutically acceptable acid addition salt thereof.

* * * * *